United States Patent [19]
Horrom et al.

[11] 4,191,760
[45] Mar. 4, 1980

[54] DIBENZODIAZEPINES

[75] Inventors: Bruce W. Horrom; William D. Barta, both of Waukegan, Ill.

[73] Assignee: Abbott Laboratories, N. Chicago, Ill.

[21] Appl. No.: 877,205

[22] Filed: Feb. 13, 1978

Related U.S. Application Data

[62] Division of Ser. No. 771,215, Feb. 23, 1977, Pat. No. 4,096,261.

[51] Int. Cl.$^2$ .................... A61K 31/55; C07D 403/04
[52] U.S. Cl. .................... 424/244; 260/239 DD; 260/239.3 T; 260/243.3; 562/435
[58] Field of Search ................ 260/239 DD; 424/244

[56] References Cited

U.S. PATENT DOCUMENTS 3,539,573  11/1970  Schmutz et al. ............. 260/239 DD

FOREIGN PATENT DOCUMENTS 1042634  9/1966  United Kingdom ............. 260/239 DD

OTHER PUBLICATIONS

DeMaio, Chem. Abstracts, vol. 72, Abstract No. 53681r, (1970).

*Primary Examiner*—Alton D. Rollins
*Attorney, Agent, or Firm*—Paul D. Burgauer; Robert L. Niblack

[57] ABSTRACT

This invention provides dibenzodiazepines represented by the formula wherein R is $-N\diagup\diagdown N-\triangleleft$, $N\diagup\diagdown N-CH_2-\triangleleft$, $N\diagup\diagdown N-CH_2C\equiv CH$, $N\diagup\diagdown N-CH_3$, $N\diagup\diagdown N-\triangleleft$, $N\diagup\diagdown N-CH_2-\triangleleft$, or $-N\diagup\diagdown N-\overset{O}{\overset{\|}{C}}H$.

The compounds of this invention are useful as antischizophrenics.

8 Claims, No Drawings

DIBENZODIAZEPINES

This is a division of application Ser. No. 771,215, filed Feb. 23, 1977, now U.S. Pat. No. 4,096,261.

DETAILED DESCRIPTION OF THE INVENTION

This invention relates to diazepines and their derivatives which are useful as antischizophrenics. The diazepines are compounds falling within the following structural formula:

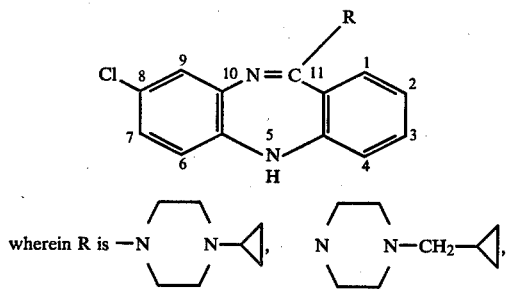

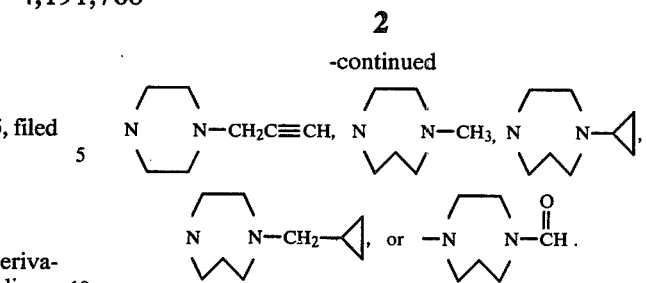

The compounds of this invention exhibit central nervous system activity as antischizophrenics. The antischizophrenic activity is obtained at dosages of from 1.0 to 15.0 mg./kg. of body weight orally and from 0.2 to 5.0 mg./kg. of body weight interperitoneally (i.p.).

The present compounds may be prepared by several techniques. Generally, as shown in Schemes (A), (B) and (C) below, the present 11-piperazinyl or 11-homopiperazinyl derivatives of the dibenzo[b,e][1,4-]diazepines may be prepared by one of the methods (A), (B) or (C) described below. In all three methods, the 8-halo substituted dibenzo diazepine-lactam (I) can be used as an intermediate to provide the desired product (III).

In the Schemes below, R is as defined above, and n is 1 or 2.

SCHEME (A)

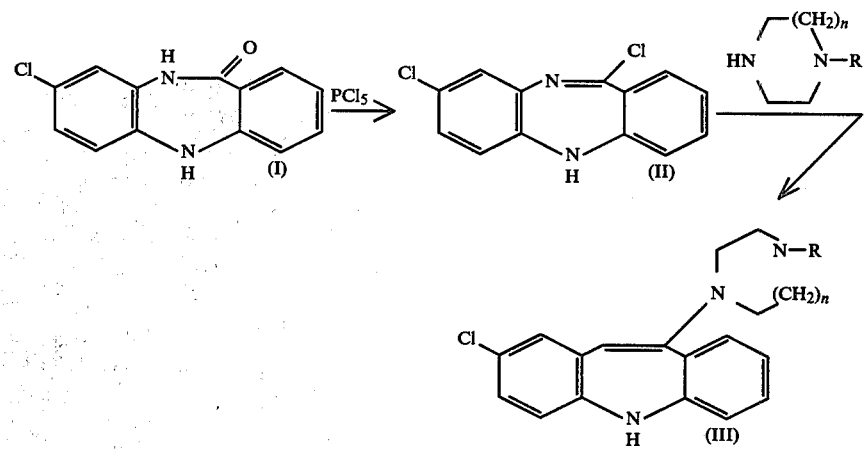

SCHEME (B)

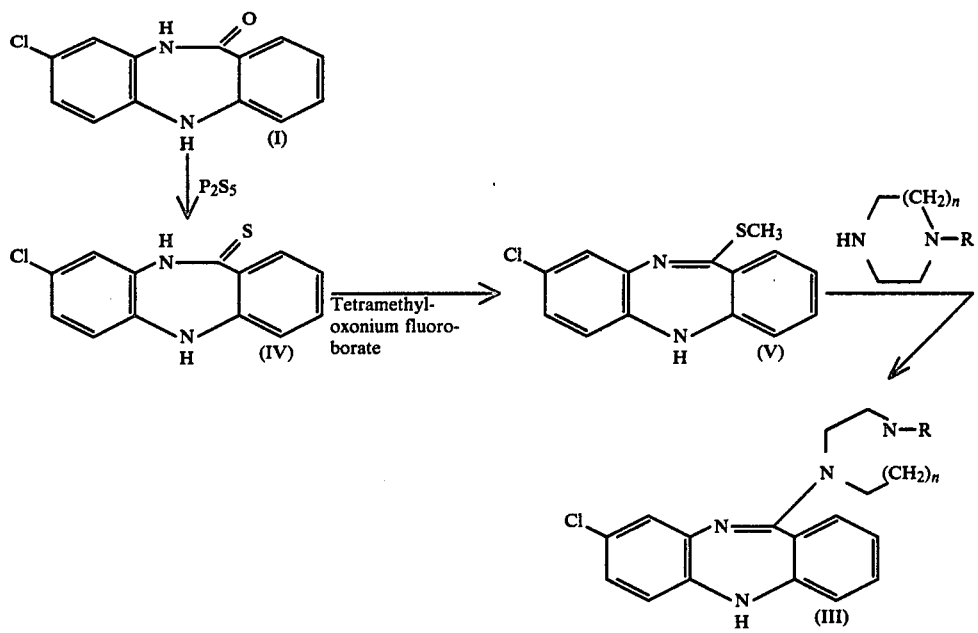

SCHEME (C)

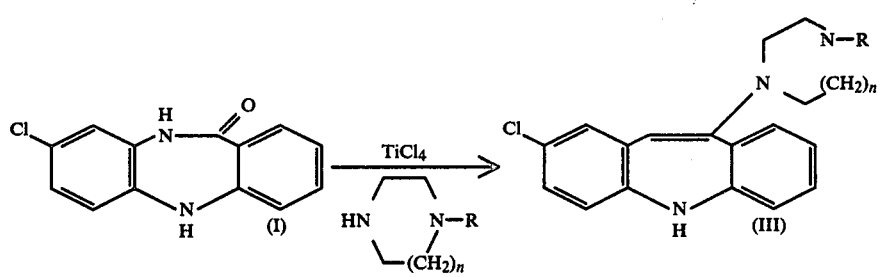

The methods as illustrated above in Schemes (A), (B) and (C) are:

Method (A)

As illustrated above, in this method, the dibenzodiazepine-lactam (1) is treated with a suitable halogenating agent such as thionyl chloride or phosphorous pentachloride and then the resulting imino-chloride (II) is reacted with the desired substituted piperazine or homopiperazine to yield product (III).

Method (B)

In this method, as illustrated in Scheme (B) above, the lactam (I) is converted to the thiolactam (IV) with phosphorous pentasulfide. Then, with a suitable alkylating agent, the thiolactam (IV) is converted to the desired imino-thio-ether (V) which is then reacted with the substituted piperazine or homopiperazine to give product (III).

Method (C)

In this method, as illustrated in Scheme (C) above, the dibenzo-diazepine-lactam (I) is reacted directly with a complex of the piperazine or homopiperazine and titanium tetrachloride to yield product (III).

The compounds that may be produced according to the present invention include:

VI. 8-Chloro-11-(4-cyclopropylmethyl piperazinyl)-5H-dibenzo[b,e][1,4]diazepine

VII. 8-Chloro-11-(4-cyclopropyl-1-piperazinyl)-5H-dibenzo[b,e][1,4]diazepine

VIII. 8-Chloro-11-(4-propargyl-1-piperazinyl)-5H-dibenzo[b,e][1,4]diazepine

IX. 8-Chloro-11-(4-cyclopropyl-1-homopiperazinyl)-5H-dibenzo[b,e][1,4]diazepine

X. 8-Chloro-11-(4-methyl-1-homopiperazinyl)-5H-dibenzo[b,e][1,4]diazepine

XI. 8-Chloro-11-(4-formyl-1-homopiperazinyl)-5H-dibenzo[b,e][1,4]diazepine

XII. 8-Chloro-11-(4-cyclopropylmethyl-1-homopiperazine)-5H-dibenzo[b,e][1,4]diazepine XIII. N-(4-Chloro-2-nitrophenyl)anthranilic acid The following examples are presented to further illustrate the present invention.

EXAMPLE 1

8-Chloro-11-(4-cyclopropylmethyl-piperazinyl)-5H-dibenzo[b,e][1,4]diazepine (VI)

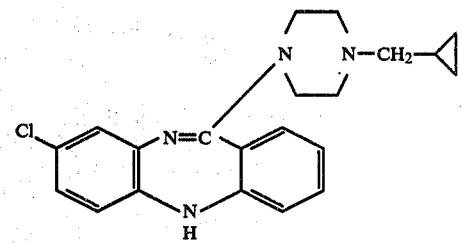

A mixture of 20.0 g. of 8-chloro-10,11-dihydro-11-oxo-5H-dibenzo[b,e][1,4]diazepine, 20.0 g. of phosphorous pentachloride and 200 ml. of dry methylene chloride was heated at reflux for one hour. The methylene chloride was evaporated in vacuo and the resulting dark residue was dissolved in 1500 ml. dry dioxane. A solution of 91 g. of cyclopropylmethyl piperazine in 400 ml. dry dioxane was added to the chloroimino intermediate over a period of 1 hour. The reaction mixture was heated at reflux for three hours. The dioxane was evaporated in vacuo and the residue was dissolved in 500 ml. toluene. The toluene was washed with 2×100 ml. water and then extracted with 4×200 ml. 10% HCl. The acid extract was washed with 100 ml. ether and then basified by being poured into a mixture of 400 ml. concentrated $NH_4OH$ and crushed ice. The basic solution was extracted with 500 ml. of ethyl acetate. The extract was washed with water and a saturated NaCl solution, dried over $Na_2SO_4$ and evaporated to dryness. The resulting foam was crystallized by triturating with anhydrous ether to give a yellow solid; m.p. 148°–151°.

Analysis Calcd. for $C_{21}H_{23}N_4$: C, 68.75; H, 6.32; N, 15.27. Found: C, 68.45; H, 6.38; N, 15.15.

EXAMPLE 2

8-Chloro-11-(4-cyclopropyl-1-piperazinyl)-5H-dibenzo[b,e][1,4]diazepine (VII)

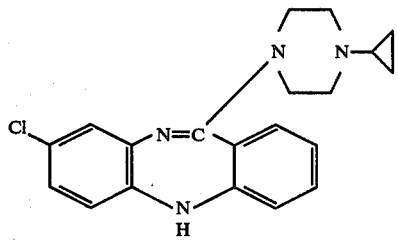

8-Chloro-11-(4-cyclopropyl-1-piperazinyl)-5H-dibenzo[b,e][1,4]diazepine was produced by the same procedure described in Example 1, above, except cyclopropyl piperazine was used in place of the cyclopropylmethyl piperazine. Same procedure gave a yellow solid; m.p. 196°–199°.

Analysis Calcd. for $C_{20}H_{22}N_4$: C, 68.08; H, 6.00; N, 15.88. Found: C, 67.75; H, 6.12; N, 15.48.

EXAMPLE 3

8-Chloro-11-(4-propargyl-1-piperazinyl)-5H-dibenzo[b,e][1,4]diazepine (VIII)

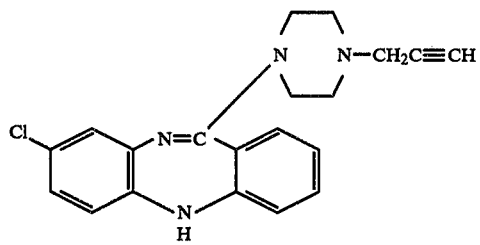

8-Chloro-11-(4-propargyl-1-piperazinyl)-5H-dibenzo[b,e][1,4]diazepine was prepared according to the procedure described in Example 1, above, except propargyl piperazine was used in place of the cyclopropylmethyl piperazine. The same procedure gave a solid; m.p. 138°–140°.

Analysis Calcd. for $C_{20}H_{19}N_4$: C, 68.47; H, 5.46; N, 15.97. Found: C, 68.18; H, 5.41; N, 15.78.

EXAMPLE 4

8-Chloro-11-(4-cyclopropyl-1-homopiperazinyl)-5H-dibenzo[b,e][1,4]diazepine (IX)

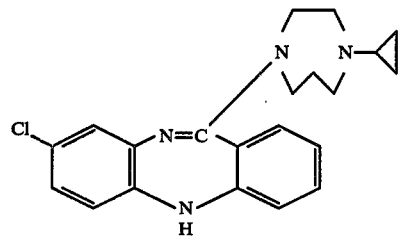

8-Chloro-11-(4-cyclopropyl-1-homopiperazinyl)-5H-dibenzo[b,e][1,4]diazepine was prepared by the same procedure described in Example 1, above, except cyclopropyl homopiperazine was used in place of the cyclopropylmethyl piperazine. The same procedure gave a yellow solid; m.p. 141°–143°.

Analysis Calcd. for $C_{21}H_{23}H_4$: C, 68.75; H, 6.32; N, 15.27. Found: C, 68.60; H, 6.39; N, 15.16.

EXAMPLE 5

8-Chloro-11-(4-methyl-1-homopiperazinyl)-5H-dibenzo[b,e][1,4]diazepine (X)

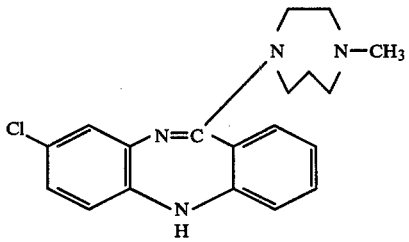

8-Chloro-11-(4-methyl-1-homopiperazinyl)-5H-dibenzo[b,e][1,4]diazepine was prepared by the same procedure described in Example 1, above, except methyl-homopiperazine was used instead of the cyclopropylmethyl piperazine. The same procedure gave a solid; m.p. 143°–145°.

Analysis Calcd. for $C_{19}H_{21}N_4$: C, 66.95; H, 6.21; N, 16.44. Found: C, 66.87; H, 6.23; N, 16.28.

EXAMPLE 6

8-Chloro-11-(4-formyl-1-homopiperazinyl)-5H-dibenzo[b,e][1,4]diazepine (XI)

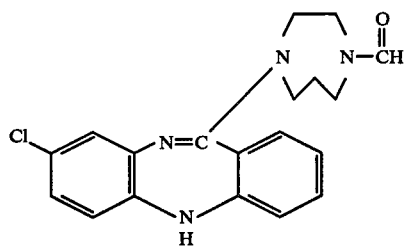

8-Chloro-11-(4-formyl-1-homopiperazinyl)-5H-dibenzo[b,e][1,4]diazepine was produced by the procedure described in Example 1, above, except formyl homopiperazine was used in place of the cyclopropylmethyl piperazine. The same procedure gave a solid; m.p. 152°–155°.

Analysis Calcd. for $C_{19}H_{19}N_4$: C, 64.31; H, 5.40; N, 15.79. Found: C, 64.00; H, 5.42; N, 15.50.

EXAMPLE 7

8-Chloro-11-(4-cyclopropylmethyl-1-homopiperazine)-5H-dibenzo[b,c][1,4]diazepine (XII)

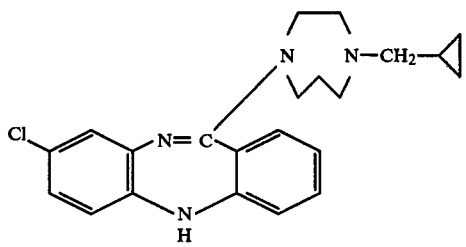

A solution of 6.15 g. cyclopropylmethyl homopiperazine in 20 ml. dry anisole is added to a stirring solution of 1.9 g. titanium tetrachloride in 50 ml. anisole at 25° C. Then 2.45 g. of 8-chloro-10,11-dihydro-11-oxo-5H-dibenzo[b,e][1,4]diazepine and 3.1 g. of cyclopropyl homopiperazine is added and the reaction mixture is heated at reflux temperature for 4 hours. The reaction mixture is allowed to cool overnight and then treated with 3 ml. isopropyl alcohol and 3 ml. 28% ammonium hydroxide. After filtration, the reaction mixture is washed with water and extracted with 10% HCl. The extract is washed with ether and then basified with 28% NH4OH. The basic solution is extracted with ether. The ether extract is washed with saturated NaCl solution, dried over $Na_2SO_4$, and evaporated to dryness. The resulting oil is purified by chromatography to give a yellow solid; m.p. 132°–134° C.

Analysis Calcd. for $C_{22}H_{25}N_4$: C, 69.37; H, 6.62; N, 14.71. Found: C, 69.09; H, 6.62; N, 14.53.

EXAMPLE 8

N-(4-Chloro-2-nitrophenyl)anthranilic acid (XIII)

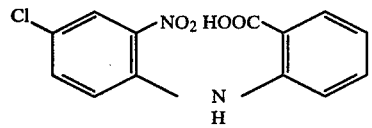

In a 3 liter, three necked round bottom flask, provided with a mechanical stirrer, reflux condenser and thermometer (to 200° C.) was placed 300 g. (1.25 m.) 1-bromo-4-chloronitrobenzene, 140 g. (1.02 m.) anthranilic acid, and 130 ml. n-amyl alcohol. The mixture was heated in an oil bath. After most of the chemicals were dissolved (80°–90° C.) the stirrer was started. Then, 1.3 gm. copper powder and 140 gm. (1.02 m.) potassium carbonate were added all at once. A yellow voluminous froth formed but no heat of reaction. As the reaction temperature rose from 80° to 120°, a red reaction mixture became more solid and hindered further stirring. The reflux condenser was replaced to distill off the formed water and amyl alcohol. Meanwhile, the temperature of the oil bath was steadily increased and finally kept at 200°–210° for 3 hours. The oil bath was replaced by a steam bath and the excess bromochloronitrobenzene was removed by steam distillation. After removal of bromochloronitrobenzene was completed, the solution was filtered and water added making the total volume of dark red solution about 2.5 liters. The solution was cooled to room temperature overnight, and filtered. Dilute HCl (1:1) was carefully added to the filtrate until it was just acid to Congo red litmus paper. The ochre-colored precipitate was removed by filtration and washed with water (750 ml.). The product was dried in vacuo at 70°. The original dark-red filter cake was digested with hot water several times and then treated as described above to extract all the desired product. Obtained: 247 grams (83% yield) of crude N-(4-chloro-2-nitrophenyl)anthranilic acid; orange granular powder; m.p. 235°–247° C.

EXAMPLE 9

8-Chloro-10,11-Dihydro-11-oxo-5-dibenzo[b,c][1,4-]diazepin (XIV)

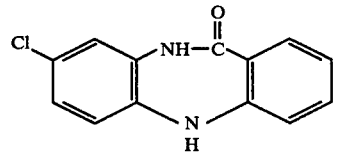

Initially, 25 g. of Raney-nickel (NiR) was prewashed by suspending it in 1000 ml. of methyl cellosolve, decanted in a solvent 3 times, and then added to a 1750 ml. stainless Parr shaker reaction vessel. To the reaction vessel (and NiR) there was added 137 g. of N-(4-chloro-2-nitrophenyl)anthranilic acid (XIII). The materials in the reaction vessel were hydrogenated on the Parr shaker under 3 atmospheres pressure until the theoretical uptake was complete. The solution was filtered and a clear dark methylcellosolve solution resulted in which there was N-(4-chloro-2-aminophenyl)anthranilic acid.

The clear dark methylcellosolve reaction solution from hydrogenation was concentrated, without further treatment, to a residue on the Rotovac. In a 3-liter, three necked round bottomed flask provided with a mechanical stirrer, condenser, Dean-Stark water separator (and heating mantle) was placed 130 gms. of crude brown N-(4-chloro-2-aminophenyl)anthranilic acid and 1500 ml. xylenes A.R. After refluxing for 90 hours, the dark reaction mixture was cooled slightly and concentrated on the Rotovac to remove the xylene. The residue was treated with 500 ml. hot water and steam distilled to remove volatile impurities. The gray-brown reaction mixture was basified with concentrated ammonia (N 4 ml.) to pH 10, and stirred for an hour. After removing some of the water on the Rotovac, the frothy mixture was cooled in an ice bath and filtered. 107 gm. of crude brown-gray powder; m.p. 223°–226°) was dissolved in about 1400 ml. acetone, and treated with Norite, filtered through a hyflosupercell material. The brown filtrate was treated with 200 ml. hot water and concentrated on the Rotovac to about 700 ml. Then, the concentrated filtrate was cooled with stirring, filtered and dried in a vacuum oven at 100° C. The filtrate was further concentrated to produce the product. 73 grams (60% yield) of 8-chloro-10,11-dihydro-11-oxo-5-dibenzo[b,c][1,4-]diazepin was obtained; m.p. 233°–236°.

EXAMPLE 10

Effect of Drug Compounds on Brain Level of Homovanillic Acid (HVA)

In testing for the effectiveness of the present drug compounds on the brain level of homovanillic acid (HVA), the drugs were administered intraperitoneally to male Long Evans rats (Simonsen) usually as aqueous solutions but in certain cases as suspensions in 0.5% methocel in 0.9% saline. The standard testing dose was 0.15 mmoles/kg body weight. The test and control groups consisted of 3-5 and 5 animals, respectively. The analyses were performed on brains (minus cerebella) removed two or three hours later. In the analyses, standard extraction and fluorimetric methods were used. The results of the analysis are set forth in the table below.

In the results, the level of brain HVA in each test group is expressed as a ratio to the level of HVA in an accompanying control group that was injected with either a 0.9% saline or a 0.5% solution of methocel. Even though ratios of less than 1.3 usually have statistical significance, only ratios greater than 1.6 are considered to be of practical significance for the pharmacological classification of drugs.

Table I

| EFFECT OF DRUG COMPOUNDS ON HVA LEVEL IN BRAIN OF RAT | | |
|---|---|---|
| Compound | HVA Level in Control Group | HVA Ratio |
| VI. | 1.0 | 3.4 |
| VII. | 1.0 | 1.1 |
| VIII. | 1.0 | 0.9 |
| IX. | 1.0 | 0.9 |
| X. | 1.0 | 1.0 |
| XI. | 1.0 | 1.0 |
| XII. | 1.0 | 0.9 |

EXAMPLE 11

Effectiveness of Drug Compound on Inhibiting Methamphetamine Antagonism in Rats Male Long-Evans black hooded rats, weighing between 100 and 150 grams, were administered the test drugs at oral doses of 5, 20 and 80 mg./kg. one hour prior to the administration of Methamphetamine at an intraperitoneal dose of 1 mg./kg. Three animals were tested at each dose level. The rats were placed in individual activity chambers equipped with photocells (Lehigh Valley, Model 1497). Antagonism of Methamphetamine induced hyperactivity was recorded as digital counts received from the photocells at one and two hour intervals. Placebo controls received a volume dose of the 0.5 carboxymethylcellulose vehicle. The data were evaluated by a one-way analysis of variance computer program. ED$_{50}$'s were calculated by the method of Litchfield and Wilcoxon (*J. Pharmacol. Exp. Therap.;* 96:99, 1949).

The results of analyses are listed in the table below. In the results, a (+) indicates a potentiation of Methamphetamine and a (−) is antagonism of Methamphetamine.

Table II

| EFFECT OF DRUG COMPOUNDS ON METHAMPHETAMINE | |
|---|---|
| Compound | Oral ED$_{50}$ (mg./kg.) |
| VI. | 80 (+) |
| VII. | 60 (−) |
| VIII. | 5 (+) |
| IX. | 5 (+) |
| X. | 9 (+) |
| XI. | 80 (+) |
| XII. | 80 (+) |

We claim:

1. A compound of the structure

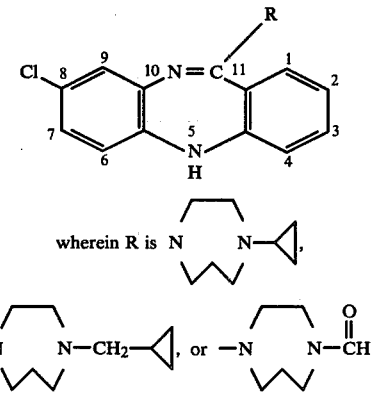

2. A compound according to claim 1, wherein R is

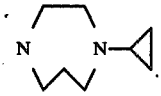

3. A compound according to claim 1, wherein R is

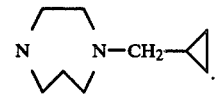

4. A compound according to claim 1, wherein R is

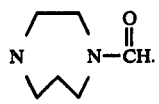
5. A composition of long lasting activity in the treatment of schizophrenics comprising as the active component an effective amount of a compound of the formula
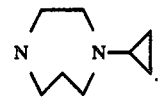
wherein R is 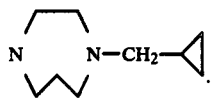,
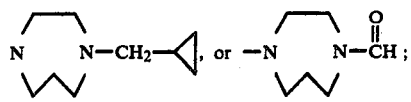
and a pharmaceutically acceptable carrier.
6. A composition according to claim 5, wherein R is
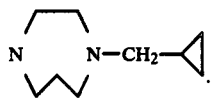
7. A composition according to claim 5, wherein R is
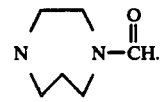
8. A composition according to claim 5, wherein R is
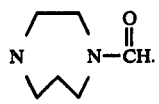
* * * * *